(12) United States Patent
Pallett et al.

(10) Patent No.: US 6,835,694 B2
(45) Date of Patent: Dec. 28, 2004

(54) HERBICIDAL COMPOSITIONS

(75) Inventors: Ken Pallett, Königstein (DE); Ashley Slater, Essex (GB)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 10/380,297

(22) PCT Filed: Sep. 17, 2001

(86) PCT No.: PCT/EP01/10692

§ 371 (c)(1),
(2), (4) Date: Oct. 2, 2003

(87) PCT Pub. No.: WO02/21919

PCT Pub. Date: Mar. 21, 2002

(65) Prior Publication Data

US 2004/0053785 A1 Mar. 18, 2004

(30) Foreign Application Priority Data

Sep. 18, 2000 (GB) ................................. 0022835

(51) Int. Cl.⁷ ..................... A01N 41/10; A01N 47/28; A01N 47/32; A01N 47/36
(52) U.S. Cl. ..................... 504/130; 504/133; 504/139; 504/144; 504/148; 504/234; 504/257; 504/263; 504/316; 504/330; 504/350
(58) Field of Search ............................. 504/130, 133, 504/139, 144, 148, 234, 257, 263, 316, 330, 350, 149

(56) References Cited

U.S. PATENT DOCUMENTS

| 4,968,342 A | 11/1990 | Forster et al. |
| 5,506,195 A | 4/1996 | Ensminger et al. |

FOREIGN PATENT DOCUMENTS

| DE | 42 16 880 A1 | 11/1993 |
| EP | 0 186 118 A2 | 7/1986 |
| EP | 0 348 737 A1 | 1/1990 |
| IT | 1224249 B1 | 9/1990 |
| JP | 07 010713 A1 | 1/1995 |
| WO | WO-95/28839 | 11/1995 |
| WO | WO-96/13163 | 5/1996 |
| WO | WO-96/17519 | 6/1996 |
| WO | WO-00/16627 A1 | 3/2000 |

OTHER PUBLICATIONS

Derwent English Language abstract of DE 42 16 880 A1.
Derwent English Language abstract of JP 07010713A.
Derwent English Language abstract of IT 1224249.

*Primary Examiner*—S. Mark Clardy
(74) *Attorney, Agent, or Firm*—Connolly Bove Lodge & Hutz LLP

(57) ABSTRACT

A method for controlling the growth of weeds at a locus which comprises applying to the locus an effective amount of: (a) a urea herbicide of general formula (1); and (b) 2-(2'-nitro-4'-methylsulfonylbenzoyl)-1,3-cyclohexanedione or an agriculturally acceptable salt or metal complex thereof.

16 Claims, No Drawings

HERBICIDAL COMPOSITIONS

This invention relates to new herbicidal compositions comprising a mixture of a benzoyl cyclohexanedione and herbicidal urea compounds. It also relates to the use of the mixture per se and to a method of controlling weeds.

Herbicidal benzoyl cyclohexanediones are disclosed in the literature, for example European Patent Publication No. 0186118. In particular, U.S. Patent Publication No. 5,506,196 discloses 2-(2'-nitro4'-methylsulfonylbenzoyl)-1,3-cyclohexanedione. Urea herbicides are well known in the literature. Examples of such herbicides include as fenuron, fluometuron, monuron and monolinuron, chlortoluron, isoproturon, diuron, linuron, neburon, methabenzthiazuron and tebuthiuron, all of which are described in "The Pesticide Manual", 12th edition, year 2000, and earlier editions (British Crop Protection Council).

The present invention provides a method for controlling the growth of weeds (i.e. undesired vegetation) at a locus which comprises applying to the locus an effective amount of:

(a) a urea herbicide, preferably a compound of the general formula (I):

$$R^{11}N(R^{12})CON(R^{13})R^{14} \quad (I)$$

wherein $R^{11}$ represents an optionally substituted cyclic hydrocarbyl (which is preferably aromatic e.g. phenyl) or aromatic heterocyclyl (e.g. thiadiazol-2-yl) group, $R^{12}$ represents hydrogen or straight or branched chain alkyl containing from 1 to 6 carbon atoms, $R^{13}$ represents straight or branched chain alkyl containing from 1 to 6 carbon atoms or an optionally substituted cyclic hydrocarbyl (e.g. 2-methylcyclohexyl) group and $R^{14}$ represents hydrogen or straight or branched chain alkyl or alkoxy containing from 1 to 6 carbon atoms; and (b) a benzoyl cyclohexanedione of formula (II):

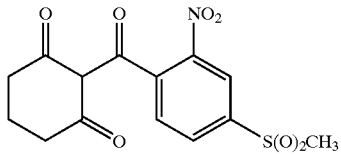

which is 2-(2'-nitro-4'-methylsulfonylbenzoyl)-1,3cyclohexanedione or an agriculturally acceptable salt or metal complex thereof.

The urea herbicide and (b) are normally used in the form of herbicidal compositions (i.e. in association with compatible diluents or carriers and/or surface-active agents suitable for use in herbicidal compositions), for example as hereinafter described.

Preferred compounds of general formula I are those wherein $R^{12}$ represents the hydrogen atom or the methyl group and $R^{13}$ represents the methyl group.

Preferred compounds of general formula I are those wherein $R^{12}$ represents the hydrogen atom, $R^{13}$ represents a phenyl, 3-trifluoromethylphenyl or 4-chlorophenyl group and $R^{14}$ represents the methyl group;

or (b) $R^{11}$ represents a 4-chlorophenyl group and $R^{14}$ represents the methoxy group, which are known respectively as fenuron, fluometuron, monuron and monolinuron, and more especially compounds of general formula I wherein $R^{12}$ represents the hydrogen atom and $R^{13}$ represents the methyl group and (c) $R^{11}$ represents a 3-chloro-4-methylphenyl or 4-isopropylphenyl group and $R^{14}$ represents the methyl group;

or (d) $R^{11}$ represents the 3,4-dichlorophenyl group and $R^{14}$ represents methyl, methoxy or butyl; or (e) $R^{11}$ represents the benzothiazol-2-yl group, $R^{12}$ represents methyl and $R^{13}$ represents methyl and $R^{14}$ represents hydrogen or (f) $R^{11}$ represents 5t-butyl-thiadiazol-2-yl; $R^{12}$ and $R^{13}$ represent methyl and $R^{14}$ represents hydrogen; which are known respectively as chlortoluron, isoproturon, diuron, linuron, neburon, methabenzthiazuron and tebuthiuron.

Preferably (a) is tebuthiuron.

In this description the term "agriculturally acceptable salts" means salts the cations or anions of which are known and accepted in the art for the formation of salts for agricultural or horticultural use. Preferably the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, formed by compounds containing an nitrogen atom with an available lone pair, include salts with inorganic acids, for example hydrochlorides, sulphates, phosphates and nitrates and salts with organic acids, for example acetic acid.

The amounts of the urea herbicide and (b) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates of from about 500 g and 2500 g of the urea herbicide and from about 0.5 g to about 512 g of (b) per hectare give good results. However, it is to be understood that higher or lower application rates may be used, depending upon the particular problem of weed control encountered.

The urea herbicide and (b) in combination may be used to control selectively the growth of weeds, for example to control the growth of those species hereinafter mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, rye, maize and rice, soya beans, field and dwarf beans, peas, lucerne, cotton, peanuts, flax, onions, carrots, oilseed rap, sunflower, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates of from about 500 g and about 2500 g of the urea herbicide and from about 5 g to about 512 g of (b) per hectare are particularly suitable.

The method described above may be used to control a very wide spectrum of annual broad-leafed weeds and grass weeds. Examples of weeds which may be controlled include:

broad-leafed weeds, for example, *Abutilon theophrasti, Amaranthus hybridus, Amaranthus retroflexus, Amaranthus rudis, Amaranthus tuberculatos, Ambrosia artemisilfolia, Ambrosia trifida, Bidens pilosa, Chenopodium album, Convolvulus arvensis, Datura ferox, Datura stramonium, Euphorbia* spp, *Galium aparine, Helianthus* spp, *Ipomoea* spp. e.g. *Ipomoea purpurea, Larnium* spp, *Matricaria* spp, *Plantago* spp, *Polygonum aviculare, Polygonum pennsylvanicum, Raphanus raphanistrum, Schkuhria*

*pinnata, Sesbania exaltata, Sida rhombifolia, Sida spinosa, Sinapis arvensis, Solanum nigrum, Veronica hederaefolia, Veronica persica,* and *Xanthium strumarium,* and grass weeds, for example *Alopecurus myosuroides, Avena fatua, Brachiaria plantaginea, Cenchrus echinatus, Cynodon dactylon, Digitaria horizontalis, Digitaria sanguinalls, Echinochloa crus-galli, Eragrostis virescens, Sorghum bicolor, Eleusine indica, Imperata cylindrica, Panicum dichotomiflorum, Panicum maximum, Panicum miliaceum, Pennisetum glaucum, Setaria* spp, e.g. *Setaria faberii, Setaria viridis, Setaria lutescens* and *Setaria italica, Sorghum halepense,* and sedges, for example, *Cyperus esculentus.*

Where the locus is an area used, or to be used, for the growth of cereal crop preferably the urea herbicid is isoproturon or chlorotoluron.

Where the locus is an area used, or to be used, for the growth of sugarcane, or for total weed control, the urea herbicide is preferably tebuthiuron.

The following table summarizes dose rate of the components generally and preferably in the method of the invention (all dose rates are in grammes per hectare (g/ha):

| Component | Crop | Timing | General | Preferred | More preferred | Most preferred |
|---|---|---|---|---|---|---|
| (b) | sugarcane | pre-em | 50–150 | 75–150 | 75–150 | 100 |
| (b) | sugarcane | post-em | 50–150 | 75–100 | 75–100 | 100 |
| Tebuthiuron | sugarcane | pre/post | 500–1500 | 1000–1500 | 1000 | 1000 |
| (b) | Total | pre/post | 75–200 | 100–150 | 100–150 | — |
| Tebuthiuron | Total | pre/post | 500–2500 | 100–2000 | 1500 | — |
| (b) | Cereal | pre-em | 50–200 | 100–200 | 150 | — |
| (b) | Cereal | post-em | 50–100 | 50–100 | 75 | — |
| Isoproturon | Cereal | pre/post | 750–2500 | 1000–2000 | 1500 | — |
| Chlortoluron | Cereal | pre/post | 1000–2000 | 1200–1600 | 1400 | — |

Where the method of the invention is used for the control of weeds at a cereal locus in a preferred embodiment (especially where (a) is isoproturon or chlortoluron) a third herbicide is provided, preferably selected from bifenox, diflufenican. When the locus is sugarcane (especially where (a) is tebuthiuron) preferred third partners include diuron and ametryne Preferred combinations include the following:

(i) from 1000 to 1500 g/ha of (a) (preferably from 1400 to 1500 g/ha); from 50 to 75 g/ha of (b) and from 100 to 150 g/ha of diflufenican;

(ii) from 1000 to 1500 g/ha of (a) (preferably about 1000 g/ha); from 50 to 75 g/ha of (b) and from 100 to 150 g/ha of diflufenican;

(iii) from 1000 g/ha of (a); from 100 to 150 g/ha of (b); and from 1000 to 1500 g/ha (preferably about 1250 g/ha) of diuron or ametryne.

The invention also provides herbicidal compositions comprising:

(a) a urea herbicide, preferably a compound of the general formula (I) above; and (b) 2-(2'-nitro4'-methylsulfonylbenzoyl)-1,3-cyclohexanedione or an agriculturally acceptable salt or metal complex thereof;

in association with an agriculturally acceptable diluent and/or carrier.

Generally the active ingredients are homogeneously dispersed in other components cited hereinafter, such as a diluent or carrier and/or surface-active agents.

The term "herbicidal compositions" is used in a broad sense, to include not only compositions which are ready for use as herbicides but also concentrates which must be diluted before use. Preferably the compositions contain from 0.05 to 90% by weight of (a) and (b).

Unless otherwise stated, the percentages and ratios appearing in the specification are by weight Generally a composition in which the ratio of (a):(b) is from 1:1 to 5000:1 wt/wt of (a):(b) is used, proportions from 1:1 to 500:1 wt/wt being preferred.

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rend red soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are wettable powders or water dispersible granules. Most preferred herbicidal compositions are aqueous suspension concentrates.

The wettable powders (or powders for spraying) usually contain from 20 to 95% of combination, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking agents and colourings.

The aqueous suspension concentrates, which are applicable by spraying, are prepared in such a way as to obtain a stable fluid product (by fine grinding) which does not settle out and they usually contain from 10 to 75% of combination, from 0.5 to 15% of surface acting agents, from 0.1 to 10% of thixotropic agents, from 0 to 10% of suitabie additives such as antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Herbicidal compositions according to the present invention may also comprise (a) and (b) in association with, and preferably homogeneously dispersed in, one or more other pesticidally active compounds and, if desired one or more compatible pesticidally acceptable diluents and carriers, surface active agents or conventional adjuvants as hereinbefore described.

Pesticidally active compounds and other biologically active materials which may be included in, or used in conjunction with, the herbicidal compositions of the present invention, for example those hereinbefore mentioned, and which are acids or bases, may, if desired, be utilized in the form of conventional derivatives, for example alkali metal and amine salts and esters.

The compositions of the invention may also contain safeners which may be useful to reduce the phytotoxicity of one or more of the pesticidally active compounds on a crop (generally where the partner pesticide is a herbicide).

The following examples illustrate herbicidal compositions for use according to the present invention. The following trade marks appear in the examples: Arkopon, Arylan, Attagel, Rhodorsil, Solvesso, Soprophor, Sopropon, Synperonic and Tixosil. The Combination listed in the following examples refers to the combination of a urea herbicide of general formula (I) and 2-(2'-nitro4'-methylsulfonylbenzoyl)-1,3-cyclohexanedione.

EXAMPLE C1

A suspension concentrate is formed from:

| | |
|---|---|
| Combination | 50% w/v |
| Antifreeze (propylene glycol) | 5% w/v |
| Ethoxylated tristyryl phenol phosphate (Soprophor FL) | 0.5% w/v |
| Nonyl phenol 9 mole ethoxylate (Ethylan BCP) | 0.5% w/v |
| Sodium polycarboxylate (Sopropon T36) | 0.2% w/v |
| Attaclay (Attagel) | 1.5% w/v |
| Antifoam (Rhodorsil AF426R) | 0.003% w/v |
| Water to 100 volumes | | by stirring the above ingredients together and milling in a bead mill.

EXAMPLE C2

An emulsifiable concentrate is formed from:

| | |
|---|---|
| Combination | 20% w/v |
| N-methylpyrrolidone (NMP) | 25% w/v |
| Calcium dodecylbenzenesulphonate (CaDDBS) (Arylan CA) | 4% w/v |
| Nonyl phenol ethylene oxide propylene oxide condensate (NPEOPO) (Synperonic NPE 1800) | 6% w/v |
| Aromatic solvent (Solvesso) to 100 volumes | | by stirring NMP, active ingredient, CaDDBS, NPEOPO and Aromatic solvent until a clear solution is formed and adjusting to volume with Aromatic solvent.

EXAMPLE C3

A wettable powder is formed from:

| | |
|---|---|
| Combination | 50% w/w |
| Sodium dodecylbenzenesulphonate (Arylan SX 85) | 3% w/w |
| Sodium methyl oleoyl taurate (Arkopon T) | 5% w/w |
| Sodium polycarboxylate (Sopropon T36) | 1% w/w |
| Microfine silicon dioxide (Tixosil 38) | 3% w/w |
| China clay | 38% w/w | by blending the above ingredients together and grinding the mixture in an air jet mill.

EXAMPLE C4

A water dispersible granule is formed from:

| | |
|---|---|
| Combination | 50% w/w |
| Sodium dodecylbenzenesulphonate (Arylan SX 85) | 3% w/w |
| Sodium methyl oleoyl taurate (Arkopon T) | 5% w/w |
| Sodium polycarboxylate (Sopropon T36) | 1% w/w |
| Binder (sodium lignosulphonate) | 8% w/w |
| China clay | 30% w/w |
| Microfine silicon dioxide (Tixosil 38) | 3% w/w | by blending the above ingredients together, grinding the mixture in an air jet mill and granulating by addition of water in a suitable granulation plant (e.g. Fluid bed drier) and drying. Optionally the active ingredient may be ground either on its own or admixed with some or all of the other ingredients.

The following non-limiting examples illustrate the invention.

EXAMPLE 1

Seed of various broad-leaf and grass weed species were sown in a non-sterilised clay loam soil. The soil surface was then sprayed with ranges of combinations of either the individual herbicide or mixtures of two herbicides in various proportions, dissolved in a mixture of acetone and water.

The said weeds are *Amaranthus spinosus, Brachiaria plantaginea, Echinochola crusgalli, Eleusine indica, Sida rhombifolia, Digitaria horizontalis* willd and *Panicum miliaceum.*

Two weeks after treatment the percent reduction in plant growth, compared to an untreated control, was assessed.

Control in one or more weed species was observed by combinations of the present invention.

EXAMPLE 2

Seed of the various weed species, as listed in Example 1, were sown and grown up to a 1-3 leaves stage. Postemergence applications with ranges of concentrations of either the individual herbicide or mixtures of two herbicides in various proportions, dissolved in a mixture of acetone and water were made.

Two weeks after treatment the percent reduction in plant growth, compared to an untreated control, was assessed.

Control in one or more weed species was observed by combinations of the present invention.

According to a further feature of the present invention there is provided a product comprising a herbicidally effective amount of:

(a) a urea herbicide of formula (I); and
(b) 2-(2'-nitro4'-methylsulfonylbenzoyl)-1,3-cyclohexanedione or an agriculturally acceptable salt or metal complex thereof; as a combined preparation for separate, simultaneous or sequential use in the control of weeds at a locus.

What is claimed is:

1. A method for controlling the growth of weeds at a locus which comprises applying to the locus an effective amount of:

(a) a urea herbicide, of the general formula (I):

$$R^{11}N(R^{12})CON(R^{13})R^{14} \qquad (I)$$

wherein $R^{11}$ represents an optionally substituted cyclic hydrocarbyl or aromatic heterocyclyl group, $R^{12}$ represents hydrogen or straight or branched chain alkyl containing from 1 to 6 carbon atoms, $R^{13}$ represents straight or branched chain alkyl containing from 1 to 6 carbon atoms or an optionally substituted cyclic hydrocarbyl group and $R^{14}$ represents hydrogen or straight or branched chain alkyl or alkoxy containing from 1 to 6 carbon atoms; and (b) a 2-(2'-nitro-4'-methylsulfonybenzoyl)-1,3-cyclohexanedione or an agriculturally acceptable salt or metal complex thereof.

2. A method according to claim 1 in which compounds of general formula I are those wherein $R^{12}$ represents the hydrogen atom or the methyl group and $R^{13}$ represents a phenyl or a methyl or a 3-trifluoromethylphenyl or 4-chlorophenyl group and $R^{14}$ represents the methyl group.

3. A method according to claim 1 in which compounds of general formula I are those wherein $R^{11}$ represents a 4-chlorophenyl group or a 3-chloro-4-methylphenyl or 3,4-dichlorophenyl or 4-isopropylphenyl group and $R^{14}$ represents a methyl or methoxy or butyl group.

4. A method according to claim 1 in which compounds of formula I are those wherein $R^{11}$ represents the benzothiazol-2-yl group, or a 5-t-butyl-thiadiazol-2-yl; $R^{12}$ and $R^{13}$ represent methyl and $R^{14}$ represents hydrogen.

5. A method according to claim 1 in which (a) is tebuthiuron.

6. A method according to claim 1, wherein from 500 g to 2500 g of (a) and from 10 g to about 500 g of (b) are applied per hectare.

7. A method according to claim 1, in which the crop is a cereal crop or sugarcane.

8. A herbicidal composition comprising:

(a) a urea herbicide as defined in claim 1 and
(b) 2-(2'-nitro-4'-methylsulfonylbenzoyl)-1,3-cyclohexanedione or an agriculturally acceptable salt or metal complex thereof, in association with a herbicidally acceptable diluent or carrier and/or surface active agent.

9. The composition according to claim 8 wherein the weight ratio of (a):(b) is from 1:1 to 5000:1.

10. The composition according to claim 8 wherein the weight ratio of (a):(b) is from 1:1 to 500:1.

11. A product comprising a herbicidally effective amount of:

(a) a urea herbicide as defined in claim 1; and
(b) 2-(2'-nitro-4'-methylsulfonylbenzoyl)-1,3-cyclohexanedione or an agriculturally acceptable salt or metal complex or mixture thereof;

as a combined preparation for separate, simultaneous or sequential use in the control of weeds at a locus.

12. A method according to claim 1, wherein (a) is selected from the group consisting of isoproturon, chiortoluron and tebuthiuron, and (a) and (b) are applied to said locus in combination with a herbicide selected from the group consisting of bifenox, diflufenican, diuron and ametryne.

13. A method according to claim 7, wherein (a) is selected from the group consisting of isoproturon, chlortoluron and tebuthiuron, and (a) and (b) are applied to said locus in combination with a herbicide selected from the group consisting of bifenox, diflufenican, diuron and ametryne.

14. A method according to claim 1 in which compounds of general formula I are those wherein $R^{11}$ represents phenyl.

15. A method according to claim 1 in which compounds of general formula I are those wherein $R^{11}$ represents thiadiazol-2-yl.

16. A method according to claim 1 in which compounds of general formula I are those wherein $R^{13}$ represents 2-methylcyclohexyl.

* * * * *